United States Patent [19]

Mavrovic

[11] 4,296,252

[45] Oct. 20, 1981

[54] UREA SYNTHESIS PROCESS

[76] Inventor: Ivo Mavrovic, 530 E. 72nd St., New York, N.Y. 10021

[21] Appl. No.: 152,534

[22] Filed: May 23, 1980

[51] Int. Cl.³ ........................................... C07C 126/02
[52] U.S. Cl. ...................................... 564/70; 564/71; 564/72
[58] Field of Search ............... 260/555 A; 564/66, 70, 564/71, 72

[56] References Cited

U.S. PATENT DOCUMENTS

| | | | |
|---|---|---|---|
| 3,579,636 | 5/1971 | Mavrovic | 260/555 A |
| 3,759,992 | 9/1973 | Mavrovic | 260/555 A |
| 3,886,210 | 5/1975 | Mavrovic | 260/555 A |
| 4,088,685 | 5/1978 | Mavrovic | 260/555 A |

*Primary Examiner*—Brian E. Hearn
*Attorney, Agent, or Firm*—Frishauf, Holtz, Goodman & Woodward

[57] ABSTRACT

An improvement in the cyclic process for producing urea wherein $CO_2$ and $NH_3$ are reacted in the presence of an aqueous ammoniacal solution in a urea synthesis reactor at an elevated temperature and at an elevated pressure in excess of 1800 PSIG to form a urea synthesis reactor effluent fluid at high pressure. The said effluent fluid is split into a minor stream and a major stream. The major stream is let down in pressure and then passed into a gas liquid separator wherein the gas stream rises through a packed midsection into the upper portion of the separator and is then taken off. The minor stream is cooled and then let down in pressure and passed into the upper portion of the gas liquid separator to produce a gas phase which is taken off from the upper portion and a liquid phase which passes down through the packed midsection and contacts the upwardly rising gas phase from the major stream wherein the downwardly passing liquid phase absorbs carbon dioxide and water vapor from said upwardly passing gaseous phase. The said liquid phase enriched in carbon dioxide and water vapor is then taken off from the lower section of the separator and withdrawn together with the liquid phase portion of the major stream. This liquid product is passed to a carbamate decomposer. The gaseous product taken from the upper section of the separator is, after further processing, at least in part recycled to the urea synthesis reactor.

3 Claims, 1 Drawing Figure

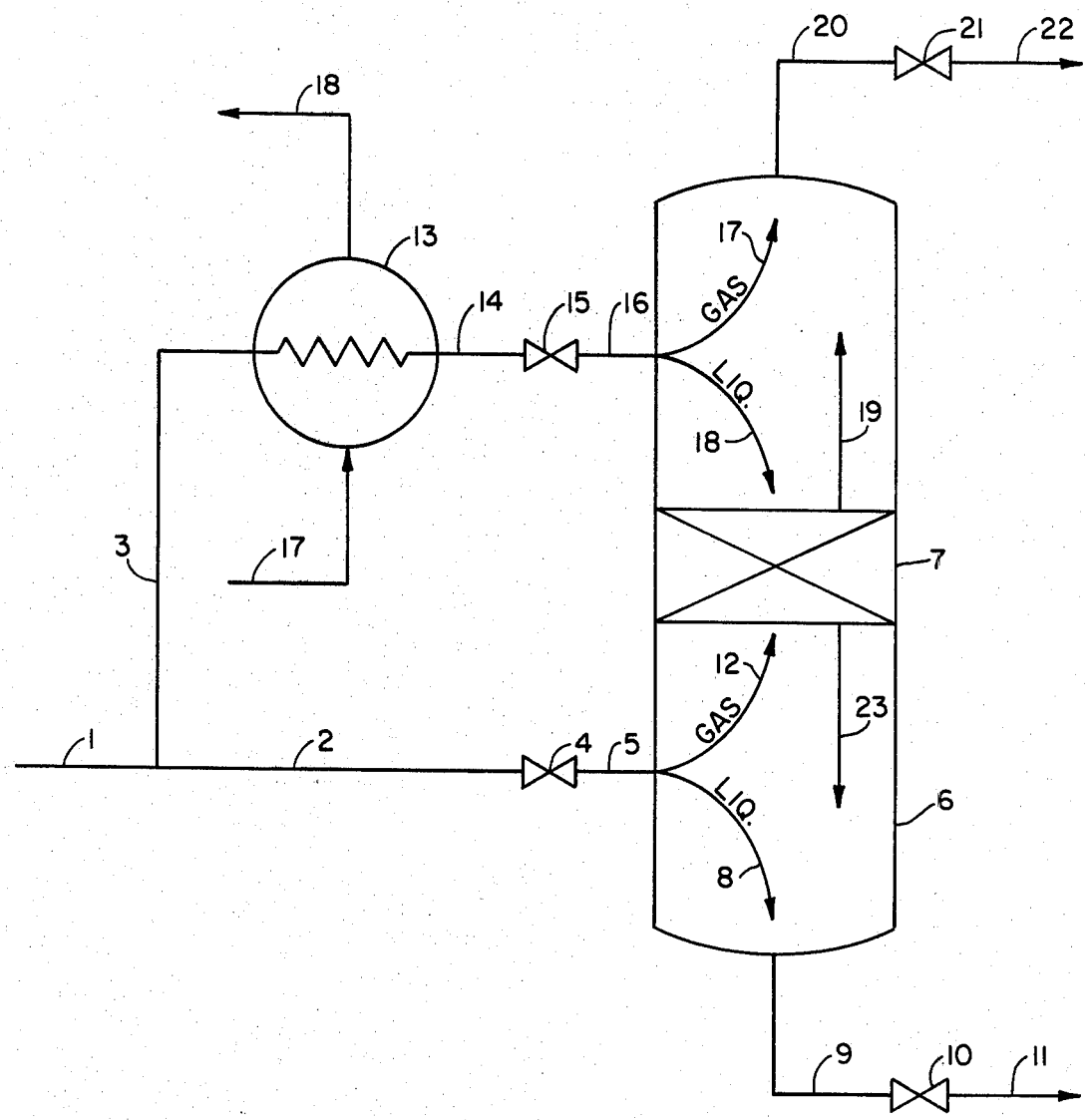

UREA SYNTHESIS PROCESS

BACKGROUND OF THE INVENTION

This invention relates to urea synthesis from ammonia and carbon dioxide, and in particular to a new method of processing the urea reactor effluent solution taken from the reactor.

Urea is conventionally synthesized by reacting ammonia and carbon dioxide in a reactor at elevated temperature and pressure to form ammonium carbamate, which, in turn, is reacted to urea and water. The first reaction of carbamate formation is very rapid and practically complete. The second reaction of urea and water formation from ammonium carbamate is slow and incomplete. In the presence of excess ammonia, i.e. above the stoichiometric amount required to form ammonium carbamate, the conversion of ammonium carbamate to urea and water is promoted. In the presence of excess water in the reactor, i.e. above the stoichiometric amount formed with the urea from ammonium carbamate, the conversion of ammonium carbamate to urea and water is hindered.

Ammonia and carbon dioxide are generally fed to the urea synthesis reactor either separately, or as an aqueous ammoniacal solution containing ammonium carbamate and/or carbonate formed by reaction of ammonia and carbon dioxide, or in a combination of separate fluid ammonia and fluid carbon dioxide with a stream of an aqueous ammoniacal solution of carbamate and/or carbonate. Generally the overall $NH_3$ to $CO_2$ molar ratio in the urea synthesis reactor is maintained between about 2.5 and 6 to one at a temperature from about 330° F. to about 400° F. and at a pressure from about 1,800 PSIG to about 6,000 PSIG.

The conversion of ammonium carbamate to urea in the urea synthesis reactor thus attained is generally in the range from about 50% to about 75%. At completion of reaction in the urea synthesis reactor, the reactor fluid is let down in pressure for the purpose of separating the aqueous urea product solution from the unconverted ammonium carbamate and from excess ammonia, both generally present in the reactor effluent. Due to the rapid adiabatic flashing of some $NH_3$, $CO_2$ and $H_2O$ from the solution after pressure reduction, the reactor effluent is cooled to about 100 to 150 degrees F below the reactor temperature. The separation of the urea product is further attained by heating the reactor effluent after adiabatic flashing at reduced pressure in a heat exchanger, generally known as decomposer. As a consequence of the heating, excess ammonia with some water vapor is driven off from the aqueous urea product solution, and the unconverted ammonium carbamate is decomposed back to ammonia and carbon dioxide gas, and the gases are expelled from the aqueous urea solution with some water vapor.

Generally the decomposer off gas containing ammonia, carbon dioxide and water vapor is condensed in a water cooled heat exchanger, and the resulting aqueous ammoniacal solution of ammonium carbamate thus formed by condensation is recycled back to the urea synthesis reactor for recovery of ammonia and carbon dioxide. In such a recirculation process, unless excess ammonia is separated before carbamate decomposition in said decomposer, an excessive amount of water vapor will result in the decomposer off gas. Consequently, an insufficient amount of water will remain available for evaporation, within the limits allowed by the internal water balance of the whole synthesis-decomposition-absorption-recirculation system, in the subsequent second stage decomposition and absorption section that usually follows the first decomposition and absorption stage for more complete recovery of unconverted reactants. Ultimately, it will not be possible to condense all the second stage decomposer off gas due to the above-described reduction in the amount of water available for condensation in the second stage condenser. If water from an external source is added to the second stage condenser for the purpose of reducing the loss of unabsorbed off gas, this amount of excess water, eventually recycled to the reactor, hinders the conversion of carbamate to urea.

In the process described in U.S. Pat. No. 3,886,210 the decomposer off gas containing $NH_3$, Carbon Dioxide and Water (stream 11 of FIG. 1.B of U.S. Pat. No. 3,886,210) is condensed in indirect heat exchange with the urea product solution being heated for the purpose of decomposing carbamate in heat exchanger 7 of said FIG. 1.B. In such a process, unless excess ammonia is separated from the reactor effluent solution at a temperature that is lower than the adiabatic flash temperature of the reactor effluent solution after let down in pressure, an excessive amount of carbon dioxide will be present in said stream of excess ammonia separated from the reactor effluent solution after let down in pressure from the reactor. As a consequence, in the subsequent step the decomposer off gas will be depleted of valuable carbon dioxide, which is the main source of heat required for exchange with the urea product solution.

In the process described in U.S. Pat. No. 3,527,799 excess ammonia is adiabatically flashed off (stream 11 of Fig. in U.S. Pat. No. 3,527,799) in Separator 10 from the residual urea effluent stream 12 before decomposition of carbamate in decomposer 13 of said figure. In said process the decomposer off gas stream 19 is condensed in heat exchanger 26 in indirect heat exchange and heat recovery with stream 25 from which carbamate is decomposed. In this process there is the drawback that too much water vapor and carbon dioxide are present in stream 11, thus depleting stream 19 of valuable water and carbon dioxide and reducing the efficiency of the heat recovery in heat exchanger 26. Moreover, the second stage off gas stream 35 will be depleted of the equivalent amount of excess water evaporated in gaseous stream 11, thus preventing total condensation and recovery of second stage decomposer off gas in condenser 36. If additional water from an external source is added to condenser 36 via stream 44, such excess water shall be recycled to the reactor 4 via streams 27, 30, 45, 52 and 6, and shall cause a reduction in conversion of carbamate to urea in said rector 4.

The process of the present invention provides a means to overcome both of said problems, namely, an excessive content of water vapor and an excessive content of carbon dioxide in the stream of excess ammonia flashed off from the reactor effluent after reduction in pressure.

THE INVENTION

The present invention provides an improved process for the treatment of reactor effluent solution after let down in pressure and before carbamate decomposition in the decomposer. The reactor effluent solution is split into minor and major streams. The gas in the major stream is separated from the liquid after pressure reduction. The minor stream is cooled and then let down in pressure, and separated into a liquid phase and a gaseous phase. The liquid phase of minor stream is sparged, after said letdown in pressure, over packing countercurrently to the gas from the major stream, thereby reducing the content of $CO_2$ and/or $H_2O$ in the gas from major stream. The two gas phases are combined and the two liquid phases are combined.

The combined overhead gas stream is further processed either analogously to stream 11 of the figure in U.S. Pat. No. 3,527,799, or by admixing it to the gas-liquid mixture in heat exchanger 21 of FIG. 1A of U.S. Pat. No. 3,886,210 for condensation and recycle to urea reactor 1 via line 59.

THE DRAWING

The drawing is an illustrative flowsheet depicting an embodiment of the present invention.

DETAILED DESCRIPTION

Referring to the drawing, the reactor effluent stream 1, withdrawn from the urea synthesis reactor (not shown), is split into a major stream 2 and in minor stream 3. Said line 1 can be either the equivalent of line 7 on the Fig. of U.S. Pat. No. 3,527,799, or the equivalent of line 2 of FIG. 1B of U.S. Pat. No. 3,886,210 issuing from reactor 1. The specification and drawings of said patents are incorporated herein by reference. Stream 3 is about 5-35% of stream 1, and preferably between about 15% and 25% of stream 1. Stream 2 is let down in pressure through valve 4 to a pressure ranging from about 30 PSIG to about 800 PSIG. Due to the reduction in pressure through valve 4, a considerable amount of $NH_3$, $CO_2$ and $H_2O$ flashes off from the reactor effluent, causing a drop in temperature in line 5. The adiabatic flash temperature in line 5 is about 100°-160° F. lower than in line 2, depending upon the overall $NH_3$ to $CO_2$ mol ratio and conversion in the urea synthesis reactor.

The mixture of gas and liquid in line 5 is delivered to separator 6, provided with a packed or tray section 7 in its upper section. The gaseous phase 12 of stream 5 is passed upward through packed or tray section 7. The urea product solution in line 11, degassed of the major part of excess ammonia is delivered to a decomposer (not shown) for heating and decomposition of unconverted carbamate contained in stream 11 to $NH_3$ and $CO_2$ gas to be separated from the residual urea product solution. Line 11 can be either the equivalent of line 12 in Fig. of U.S. Pat. No. 3,527,799, or the equivalent of line 6 of FIG. 1B of U.S. Pat. No. 3,886,210.

The minor stream 3 is cooled in heat exchanger 13 to a temperature in line 14 from about 40° F. to about 80° F. lower than in line 3. The cooling medium is delivered to cooler 13 through line 17, and withdrawn through line 18. The cooling medium can be cooling water, liquid ammonia, carbamate solution, urea solution or a combination of the above fluids. Cooled stream 14 is reduced through valve 15 to substantially the same pressure prevailing in line 5 and vessel 6.

Due to the reduction in pressure through valve 15, a considerable amount of excess ammonia with a minor content of $CO_2$ and water vapor flashes off from stream 14, causing a decrease in temperature in line 16 by about 100°-160° F., depending upon the overall molar ration of $NH_3$ to $CO_2$ and ammonium carbamate conversion to urea in the urea synthesis reactor. Because the minor stream 3 is cooled in cooler 13 before let down in pressure through valve 15, the temperature of the adiabatic flash mixture in line 16 is about 50°-80° F. lower in temperature than the adiabatic flash mixture in line 5.

The mixture of gas and liquid in line 16 is delivered into separator 6 above its packed or tray section 7. The gaseous stream 17 of stream 16 is discharged overhead through line 20. The liquid stream 18 of stream 16 is sparged over the top of packed or tray section 7. Because the mixture in line 16 is at a lower temperature than the mixture in line 5, the gaseous stream 17, separated from stream 16, contains much less $CO_2$ and $H_2O$ than the gaseous stream 12, separated from stream 5. Liquid stream 18, separated from stream 16, flows downwards through packed or tray section 7 and countercurrently to gaseous stream 12, 50°-80° F. hotter than liquid stream 18. Due to the direct countercurrent contact of colder liquid stream 18 with hotter gaseous stream 12, the latter is cooled by 10°-20° F., whereas liquid stream is heated by 30°-40° F.

As gaseous stream 12 is gradually cooled in packed section 7 in its upward flow, a portion of the water vapor and $CO_2$ gas contained in stream 12 when it enters the packed section 7 is condensed and reacts with ammonia, respectively, and is dissolved in the downcoming liquid stream 18. The heat of reaction released in packed section 7 is transferred to the downcoming liquid stream 18, causing its temperature to rise. The cooled gaseous stream 12 emerges from the top of packed section 7 as stream 19, with a lower content of $CO_2$ and $H_2O$ than gaseous stream 12. Liquid stream 18 leaves the bottom of packed section 7 as stream 23, enriched in $CO_2$ and $H_2O$.

Stream 23 is mixed with stream 8 and discharged through bottom line 9, valve 10 and line 11 for further processing, as for instance, analogously to stream 6 of FIG. 1B of U.S. Pat. No. 3,886,210. Gaseous stream 19 is mixed with stream 17, and discharged overhead through line 20, valve 21 and line 22 for further processing and recycling to the reactor for recovery, as for instance by delivering said stream 22 to condenser 21 of FIG. 1A of U.S. Pat. No. 3,886,210 for condensation and delivery to reactor 1 for recovery. The gaseous stream 20 has a lower concentration of $H_2O$ and $CO_2$ than gaseous stream 12, and liquid stream 9 has a higher concentration of $H_2O$ and $CO_2$ than stream 8. For this reason, less water is recycled back to the reactor via stream 20, and more $H_2O$ and $CO_2$ is available in the subsequent steps of carbamate decomposition (not shown) and formation of the decomposer off gas stream with a higher concentration of $H_2O$ and $CO_2$. The latter is very important in the process of decomposer off gas condensation in indirect contact and heat recovery with a process stream to be heated, as for example in said U.S. Pat. Nos. 3,759,992 and 3,886,210.

The process of the present invention is further illustrated by the following example.

EXAMPLE 180,236 lbs/hr of reactor effluent at 375° F. and 3,100 PSIG flow through line 1. Said line 1 can be either the equivalent of line 7 on the Fig. of U.S. Pat. No. 3,527,799, or the equivalent of line 2 of FIG. 1of U.S. Pat. No. 3,886,210 issuing from reactor 1. It has the following composition: 11.49 wt% $CO_2$, 36.62 wt% of $NH_3$, 18.60 wt% $H_2O$ and 33.29 wt% urea. 20% of said fluid in line 1 is passed through line 3, and the remaining 80% through line 2. The fluid in line 2 is let down in pressure through valve 4 to 300 PSIG. Due to reduction in pressure, gas flashes off from the solution. Due to said flashing, the temperature of the fluid in line 5 decreases to 255° F. The fluid from line 5 is discharged into separator 6 below packed section 7, and separated into gaseous stream 12 and liquid stream 8. Liquid stream 8 is collected in the bottom section of separator 6. Gaseous stream 12 is passed into packing 7 and has the following composition: 11.32 wt% $CO_2$, 81.81 wt% $NH_3$ and 6.87 wt% $H_2O$, countercurrently to the liquid phase flowing downwards through packing 7.

The fluid in line 3 is cooled to 310° F. in cooler 13. In said cooler 13 a stream of weak ammoniacal solution of ammonium carbamate containing some urea, acting as a cooling medium for stream 3, is received from line 17 at 105° F. and exited from cooler 13 at 220° F. through line 18. The fluid in line 14 which is at 310° F. and 3,100 PSIG is let down in pressure through valve 15 to 300 PSIG. Analogously to the stream in line 5, described above, due to reduction in pressure, gas flashes off from the solution to form gaseous stream 17 having the following composition: 8.02 wt% $CO_2$, 89.97 wt% $NH_3$ and 2.01 wt% $H_2O$. Due to said flashing, the temperature of the liquid in line 16 decreases to 200° F.

Stream 17 contains 30% less $CO_2$ and 71% less $H_2O$ than stream 12.

Stream 18 separated from gaseous stream 17 is sparged over packed section 7 and passed downward through packing 7 countercurrently to gaseous stream 12, rising through packing 7. Stream 12 is cooled in packing 7 to about 220° F. and emerges from packing 7 as stream 19 with a lower concentration of $CO_2$ and $H_2O$ than stream 12. Stream 19 is mixed with stream 17 and withdrawn through line 20 at the following overall composition: 9.06 wt% $CO_2$, 88.93 wt% $NH_3$ and 2.01 wt% $H_2O$. Stream 20 contains a lower concentration of $CO_2$ and $H_2O$ than stream 12. If stream 3, cooler 13, and packed section 7 were eliminated, stream 20 would have the same composition as said stream 12, at a considerable increase in $CO_2$ and water concentration. Stream 20 is passed through regulating valve 21 and through line 22 for further processing either analogously to stream 11 of the Fig. in U.S. Pat. No. 3,527,799, or for instance delivered directly to heat exchanger 21 of FIG. 1A of U.S. Pat. No. 3,886,210 through line 58, for condensation and recycle to urea reactor 1 via stream 59.

Liquid stream 18 is heated in packed section 7 to about 245° F., enriched in $CO_2$ and $H_2O$ and as stream 23 mixed with liquid stream 8. Combined stream 9 is withdrawn from the bottom section of separator 6 and delivered through valve 10 and line 11 to a decomposer (not shown) for further processing, for instance either analogously to stream 12 in the Fig. in U.S. Pat. No. 3,527,599 and the process scheme described therein, or analogously to stream 6 of FIG. 1B of U.S. Pat. No. 3,886,210 and the process scheme described therein passed into predecomposer 7 and through line 8 to decomposer 9 for carbamate decomposition. In the latter case, a minor portion of stream 6 can be delivered through line 20 to the top tray section 16 of separator 15 to replace stream 3 split from stream 2, as described in U.S. Pat. No. 3,886,210.

Various changes and modifications may be made and features described in connection with any one of the embodiments may be used with any of the others within the scope of the inventive concept.

I claim:

1. In a cyclic process for producing urea comprising reacting $CO_2$ and $NH_3$ in the presence of an aqueous ammoniacal solution of at least one compound selected from the group consisting of ammonium carbonate and/or ammonium carbamate in a urea synthesis reactor at an elevated temperature of about 330° F. to about 400° F. and at a pressure from about 1,800 PSIG to about 6,000 PSIG, to form a urea synthesis reactor effluent fluid at high pressure, lowering the pressure of said reactor effluent fluid to flash off gaseous $NH_3$, $CO_2$ and $H_2O$ phase to obtain a residual reactor effluent solution comprising ammonium carbamate, ammonia, water and urea, recycling at least part of said flashed off gaseous $NH_3$, $CO_2$ and $H_2O$ phase to the urea reactor, passing said residual reactor effluent solution to a carbamate decomposer wherein it is heated and wherein the ammonia and water vapor contained in said effluent solution is taken off in a gaseous product and wherein the ammonium carbamate is decomposed to form gaseous ammonia and gaseous carbon dioxide which is also taken off in the gaseous product, at least part of said gaseous product from said carbamate decomposer is recycled to said urea synthesis reactor, and a liquid product solution is withdrawn from said carbamate decomposer containing urea, the improvment comprising splitting said urea synthesis reactor effluent fluid stream into a minor stream containing from about 5% to about 35% by weight of the total urea synthesis reactor effluent fluid stream, and a major stream containing the balance of said urea reactor effluent fluid stream, passing said major stream through a pressure release valve to lower the pressure to the range from about 30 PSIG to about 800 PSIG and then passing said major stream at said lower pressure to the lower section of a liquid gas separator having a midsection provided with a liquid gas contact means above said lower section and an upper section above said midsection, said major stream at said lower pressure comprising (i) a gaseous phase containing $NH_3$, $CO_2$ and $H_2O$ which rises into and through said midsection of said separator into said upper section, and is removed therefrom with the other gaseous contents thereof, and (ii) a liquid phase containing urea and unconverted ammonium carbamate which passes downthrough the lower section of said separator and is withdrawn as a liquid part of the liquid product from the separator which is passed to an ammonium carbamate decomposer, passing said minor stream through a heat exchanger wherein its temperature is lowered between about 40° and 80° F., and then passing said cooled minor stream through a pressure release valve to lower the pressure to substantially the pressure of the major stream as it enters said liquid gas separator and passing said minor stream having said lowered pressure to the upper section of said liquid gas separator wherein it is separated into (a) a gaseous phase containing $NH_3$, $CO_2$ and $H_2O$ which is removed therefrom with the other gaseous contents of said upper section of said separator and recycled to said urea synthesis reactor and (b) a liquid phase which is passed downwardly through said midsection of said separator wherein it contacts the gaseous phase (i) passing upward through said midsection and absorbs carbon dioxide and water vapor from said gaseous phase (i) and said liquid phase (b) then passes downwardly through the lower section of said separator and is withdrawn as part of the liquid product from the separator which is passed to said ammonium carbamate decomposer, whereby the combined gaseous phase from said liquid separator which is recycled to said urea synthesis reactor has a lower $CO_2$ and $H_2O$ content than said gaseous phase (i) flashed off from said major stream and rising into and through said midsection of said separator, and the combined liquid product withdrawn from the lower section of said separator containing ammonium carbamate which is passed to said carbamate decomposer, has a larger content of $CO_2$ and $H_2O$ than the liquid phase (ii) of said major stream after reduction in pressure and before passing through the lower section of said separator and mixing with the liquid phase (b) of said minor stream passed downwardly through said midsection of said separator.

2. The process of claim 1 wherein only a part of said gaseous phase discharged from said gas separator is recycled to said urea synthesis reactor.

3. The process of claim 1 wherein only a part of the gaseous phase from said carbamate decomposer is recycled to said urea synthesis reactor.

* * * * *